(12) United States Patent
Worley et al.

(10) Patent No.: US 8,821,907 B2
(45) Date of Patent: Sep. 2, 2014

(54) BIOCIDAL N-HALAMINE EPOXIDES

(75) Inventors: Shelby D. Worley, Auburn, AL (US); Jie Liang, Auburn, AL (US); Yongjun Chen, Bellevue, WA (US); Royall M. Broughton, Valley, AL (US); Jia-Wang Wang, Jinan (CN); Rong Wu, Auburn, AL (US); Unchin Cho, Edina, MN (US); Jaewoong Lee, Auburn, AL (US); Kevin Barnes, Opelika, AL (US)

(73) Assignee: Auburn University Office of Technology Transfer, Auburn, AL (US)

( * ) Notice: Subject to any disclaimer, the term of this patent is extended or adjusted under 35 U.S.C. 154(b) by 2223 days.

(21) Appl. No.: 11/373,458

(22) Filed: Mar. 10, 2006

(65) Prior Publication Data

US 2007/0015921 A1    Jan. 18, 2007

Related U.S. Application Data

(60) Provisional application No. 60/660,819, filed on Mar. 11, 2005.

(51) Int. Cl.
*A01N 25/00* (2006.01)
*A01N 65/00* (2009.01)
*A61Q 17/00* (2006.01)

(52) U.S. Cl.
CPC ............. *A01N 65/00* (2013.01); *A61Q 17/005* (2013.01)
USPC ......................................................... 424/405

(58) Field of Classification Search
CPC ............................ A61Q 17/005; A01N 65/00
USPC ......................................................... 424/405
See application file for complete search history.

(56) References Cited

U.S. PATENT DOCUMENTS

| | | | |
|---|---|---|---|
| 2,985,501 A | 5/1961 | Gagarine | 8/120 |
| 3,846,442 A | 11/1974 | Habermeier et al. | 260/309.5 |
| 3,979,477 A | 9/1976 | Schmid et al. | 260/835 |
| 4,206,104 A | 6/1980 | Dowbenko et al. | 260/29.3 |
| 4,668,273 A * | 5/1987 | Haase | 504/155 |
| 5,194,504 A | 3/1993 | Lebovits et al. | 525/131 |

(Continued)

FOREIGN PATENT DOCUMENTS

| | | | |
|---|---|---|---|
| CH | 1368080 | 9/1974 | C07D 49/32 |
| JP | 54-29400 | 3/1979 | C08G 73/06 |

OTHER PUBLICATIONS

N. Nurdin et al., "Biocidal Polymers Active by Contact. II. Biological Evaluation of Polyurethane Coatings with Pendant Quaternary Ammonium Salts," Journal of Applied Polymer Science, vol. 50, 1993, pp. 663-670.

(Continued)

*Primary Examiner* — Benjamin Packard
(74) *Attorney, Agent, or Firm* — Haverstock & Owens LLP

(57) ABSTRACT

N-halaminehydantoinyl epoxide compounds which can be used for the construction of coatings and materials which can be rendered biocidal by exposure to halogen solutions either before or after curing the coating or material are disclosed. The biocidal coatings and materials can then be used to inactivate pathogenic microorganisms such as bacteria, fungi, and yeasts, as well as virus particles, which can cause infectious diseases, and those microorganisms which cause noxious odors and unpleasant coloring such as mildew. The coatings are compatible with a variety of substrates including, but not limited to, cellulose, chitin, chitosan, synthetic fibers, cement grout, latex caulk, acrylic films, polyurethanes, plastics and paints.

13 Claims, 3 Drawing Sheets

(56) References Cited

U.S. PATENT DOCUMENTS

| | | | | |
|---|---|---|---|---|
| 5,463,058 | A | 10/1995 | Carrozza et al. | 546/14 |
| 5,490,983 | A | 2/1996 | Worley et al. | 424/405 |
| 5,882,357 | A | 3/1999 | Sun et al. | 8/189 |
| 5,902,818 | A | 5/1999 | Worley et al. | 514/376 |
| 6,770,287 | B1 | 8/2004 | Sun et al. | 424/404 |
| 6,969,769 | B2 | 11/2005 | Worley et al. | 548/110 |
| 2003/0056297 | A1 | 3/2003 | Sun | 8/115.51 |

OTHER PUBLICATIONS

N. Nurdin et al., "Biocidal Polymers Active by Contact, III. Ageing of Biocidal Polyurethane Coatings in Water," Journal of Applied Polymer Science, vol. 50, 1993, pp. 671-678.

G. Sun et al., "A New Cyclic $N$-Halamine Biocidal Polymer", Ind. Eng. Chem. Res. vol. 33, No. 1, 1994, pp. 168-170.

G. Sun et al., "Performance of a New Polymeric Water Disinfectant," Water Resources Bulletin, vol. 32, No. 4, Aug. 1996, pp. 793-797.

G. Sun et al., "Disinfection of Water by $N$-Halamine Biocidal Polymers," Ind. Eng. Chem. Res. vol. 34, No. 11, 1995, pp. 4106-4109.

V. S. Panangala et al., "Inactivation of Rotavirus by New Polymeric Water Disinfectants," Journal of Virological Methods 66 (1997), pp. 263-268.

S. D. Worley et al., "Biocidal Polymers," TRIP vol. 4, No. 11, Nov. 1996, pp. 365-370.

S. D. Worley et al., "Disinfection of Water by $N$-Halamine Biocidal Polymers," HaloSource Corporation, Jul. 1997, 3 pages.

J. Lin et al., "Antimicrobial Treatment of Nylon," Journal of Applied Polymer Science, vol. 81, 2001, pp. 943-947.

J. Lin et al., "Biocidal Polyester," Journal of Applied Polymer Science, vol. 85, pp. 177-182, 1996.

\* cited by examiner

BIOCIDAL N-HALAMINE EPOXIDES

RELATED APPLICATIONS

This application claims priority under 35 U.S.C. §119(e) of the U.S. Provisional Application Ser. No. 60/660,819, titled "Biocidal N-Halamine Epoxides", filed Mar. 11, 2005. The U.S. Provisional Application Ser. No. 60/660,819, titled "Biocidal N-Halamine Epoxides", filed Mar. 11, 2005, is hereby incorporated by reference.

FIELD OF THE INVENTION

The invention relates to methods of attaching biocides onto surfaces and/or incorporating biocides into materials. More specifically, this invention relates to methods for attaching biocidal N-Halamine structures onto surfaces and/or incorporating them into materials.

BACKGROUND

Previous attempts to incorporate biocidal activity into materials and coatings have primarily involved two methods—physical mixing (blending) of biocides into the materials and coatings, and chemical binding of biocidal functional groups to the polymers or copolymers comprising the materials and coatings. Chemical binding should be preferable for long-term biocidal activity if the bound biocidal functionality does not adversely affect the other desired properties such as strength, appearance, and chemical resistance of the material or coating. For example, a significant amount of work has been performed concerning rendering sponges biocidally active. This involves encapsulation of a variety of weak biocides into the porous structure of the sponge, either through physical blending or chemical bonding to the surface. The sponges modified in this manner can exhibit biocidal activity, but the contact times necessary for action are generally long, and some pathogens are not inactivated even at contact times of several hours. Anti-fouling polyurethanes have been prepared by chemical incorporation of tributyl tin as described in U.S. Pat. No. 5,194,504, and quaternary ammonium salts (see for example, *J. Appl. Polym. Sci.* 50: 663 (1993); *J. Appl. Polym. Sci.* 50: 671 (1993)). Coatings containing organo tin compounds are being discredited as threats to the environment, and poly-quats are weak biocides which are nonregenerable.

Poly-1,3-dichloro-5-methyl-5-(4'-vinylphenyl)hydantoin is a non-toxic, non-irritating, polymer that has been described in U.S. Pat. No. 5,490,983, which has been shown to exhibit biocidal properties (see *Ind. Eng. Chem. Res.* 33:168 (1994); *Water Res. Bull.* 32:793 (1996); *Ind. Eng. Chem. Res.* 34:4106 (1995); *J. Virolog. Meth.* 66:263 (1997); *Trends in Polym. Sci.* 4:364 (1996); *Water Cond. & Pur.* 39:96 (1997)). This polymer is effective against a broad spectrum of pathogens including *Staphylococcus aureus, Pseudomonas aeruginosa, Escherichia coli, Candida albicans, Klebsiella terrigena*, poliovirus, and rotavirus, among others, causing large log reductions in contact times of the order of a few seconds in water disinfection applications.

Compounds with N-Halamine functional groups such as hydantoins, oxazolidinones, and imidazolidinones have also been employed recently in producing biocidal cellulose (U.S. Pat. No. 5,882,357), biocidal films on surfaces (U.S. Pat. Nos. 5,902,818 and 6,969,769), biocidal Nylon (Lin et al., J. Appl. Polym. Sci., 81, 943 (2001)), and biocidal polyester (Lin et al., J. Appl. Polym. Sci., 85, 177 (2002)). The U.S. Pat. Nos. 5,882,357 5,902,818 and 6,969,769 and the Articles Lin et al., J. Appl. Polym. Sci., 81, 943 (2001) and Lin et al., J. Appl. Polym. Sci., 85, 177 (2002) are all hereby incorporated by reference. However, these N-Halamine-based biocides have limited applications for coating materials.

Because of the aforementioned environmental hazards of tin-based biocidal materials and the limited application of the previously known N-Halamine biocidal materials, there is a continued need for more effective biocidal coatings and materials.

SUMMARY

The present invention is directed to using N-halamines in biocidal coatings and/or in the fabrication of materials. In accordance with the embodiments of the invention the N-halamines are N-halamine hydantoinyl epoxide compounds that are synthesized and used for the construction of biocidal coatings and materials. The N-halamine hydantoinyl epoxide compounds are preferably attached to a surface or material through a ring opening mechanism of the epoxide portion of the N-halamine hydantoinyl epoxide.

The biocidal coatings and materials made in accordance with the embodiments of the invention inactivate pathogenic microorganisms such as bacteria, fungi, and yeasts, as well as virus particles, which can cause infectious diseases, and those microorganisms that cause noxious odors and unpleasant coloring such as mildew. The coatings can be made that are compatible with a variety of substrates including, but not limited to, cellulose, chitin, chitosan, synthetic fibers, cement grout, latex caulk, acrylic films, polyurethanes, plastics, and paints.

UK Patent No. 1,368,080 describes producing epoxy resins containing unhalogenated poly-glycidylhydantoin compounds for the purpose of producing molded shapes with good electrical and mechanical properties but fails to teach halogenation of such derivatives before or after bonding to a surface to render the surface biocidal. The compound 3-glycidyl-1,3,8-triaza-7,7,9,9-tetramethylspiro[4.5]decane-2,4-dione (such as shown in FIG. 1B and unhalogenated) has been employed as a light stabilizer for polymers (Japanese Patent No. 1977-94808), but a method of making materials with biocidal activity is neither taught nor suggested.

DETAILED DESCRIPTION OF THE INVENTION

Figure 1A:
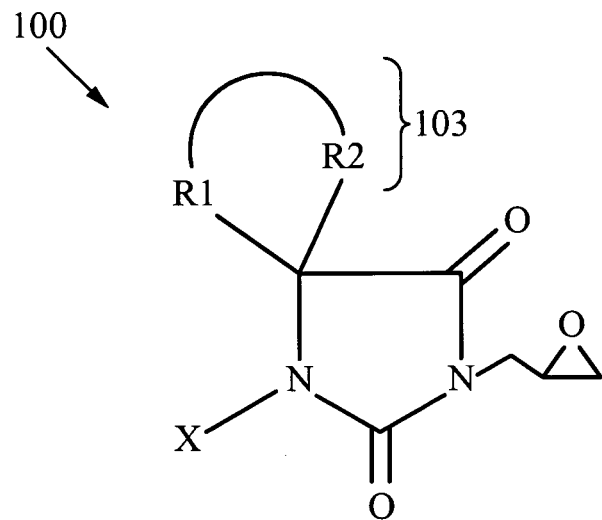
FIGS. 1A-B show structures of N-Halamine hydantoinyl epoxide compounds.
Figure 1B:
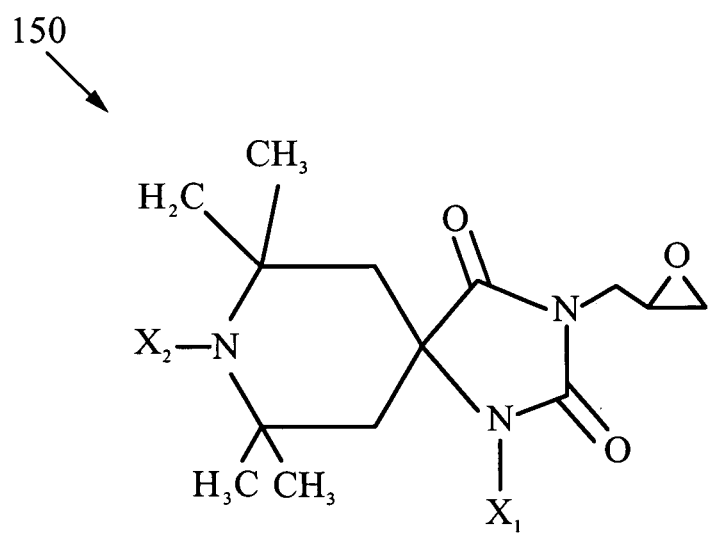

N-halamines are in accordance with the preferred embodiment of the invention N-halamine hydantoinyl epoxide compounds 100 and 150, such as shown in FIGS. 1A-B. In accordance with this preferred embodiment, one or more N-halamine hydantoinyl epoxide compounds 100 and 150 are synthesized and used for fabricating biocidal coatings and/or materials. Preferably, the hydantoinyl portion of the N-halamine hydantoinyl epoxide is halogenated, either before or after adding them to materials and/or attaching them to a surface of a material in order to render them biocidal. Herein "unhalogenated compounds" refers to the compounds 100 and 150 wherein X, $X_1$, and $X_2$ are H and "halogenated compounds" refers to the structures 100 and 150, wherein X, $X_1$, and $X_2$ are Cl or Br. Herein, "the functionalized surface or material" refers to a surface or material that bound N-halamine hydantoinyl moieties. Preferably, the N-halamine hydantoinyl moieties bind to the surface or material through a condensation reaction of the epoxide portion of the N-halamine hydantoinyl epoxide compounds, such as described below with reference to FIGS. 3A-B.

Referring to FIG. 1A, where the N-halamine hydantoinyl epoxide has a structure represented by 100, $R_1$ and $R_2$ are $C_1$-$C_8$ alkyl, cycloalkyl, and phenyl groups or alternatively are a spiropentamethylene or other cyclic structure 103. Preferably, X is one of H, Cl and Br group. When $R_1$ and $R_2$ are both methyl groups, then X is preferably one of a Cl and a Br group.

Referring to FIG. 1B, where the N-halamine hydantoinyl epoxide has a structure represented by 150, $X_1$ and $X_2$ are a H, Cl, and Br groups or a mixture thereof. However, preferably only one of $X_1$ and $X_2$ is H. As described above, preferably the halogenated versions of the N-halamine hydantoinyl epoxide compounds 100 and 150 are used to make biocidal coatings and/or materials.

Figure 2:
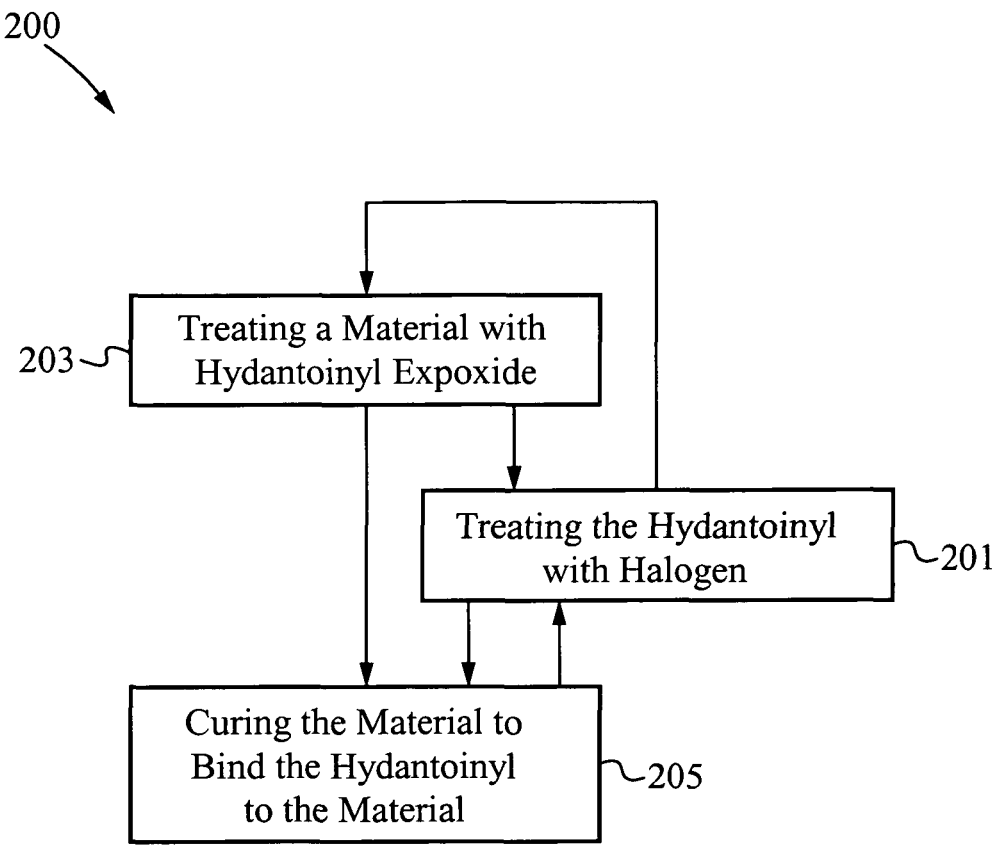
FIG. 2 is a block diagram outlining the steps of the method for making a biocidal material, in accordance with the embodiments of the invention.

FIG. 2 is a block diagram 200 outlining the steps of a method of making a composition with biocidal activity, in accordance with the embodiments of the invention. In the step 203, one or more materials are treated with one or more of the N-halamine hydantoinyl epoxide compounds 100 and 150 (FIGS. 1A-B). After the one or more materials are treated with one or more of the N-halamine hydantoinyl epoxide compounds 100 and 150 in the step 203, in the step 205, the mixture of the one or more N-halamine hydantoinyl epoxide compounds and/or the one or more materials is cured by, for example, heating the mixture or exposing the mixture to microwave radiation to generate a functionalized material or materials, such as described below with reference to FIGS. 3A-B. After the mixture of the one or more N-halamine hydantoinyl epoxide compounds and the one or more materials is cured to generate the functionalized material or materials in the step 205, in the step 201 the functionalized material or materials is are treated to a oxidizing halogen agent in order to halogenate the nitrogen atoms and render the composition biocidal.

Still referring to FIG. 2, in accordance with alternative embodiments of the invention, the one or more N-halamine hydantoinyl epoxide compounds are halogenated in the step 201, prior to the step 203 of treating the one or more materials with the one or more of the N-halamine hydantoinyl epoxide compounds. In still further embodiments of the invention, the hydantoinyl portions of the one or more N-halamine hydantoinyl epoxide compounds are halogenated after the step 205 of curing the mixture, such that the functionalized material or materials that are formed in the step 205 are biocidal. In any case, as described above, it is preferable at some point that the hydantoinyl portions of the one or more N-halamine hydantoinyl epoxide compounds are halogenated to optimize the biocidal activity of the composition formed. It will be clear to one skilled in the art that the step 201 of halogenating can be performed multiple times during the fabrication of the biocidal composition.

The material or materials used to make a biocidal composition in accordance with the method of the invention can include, but are not limited to, cellulose, chitin, chitosan, synthetic fibers, cement grout, latex caulk, acrylic film, polyurethane, plastics and paint. The biocidal composition formed can be used directly, that is applied directly to a surface and/or used as an additive to other materials.

Figure 3A:
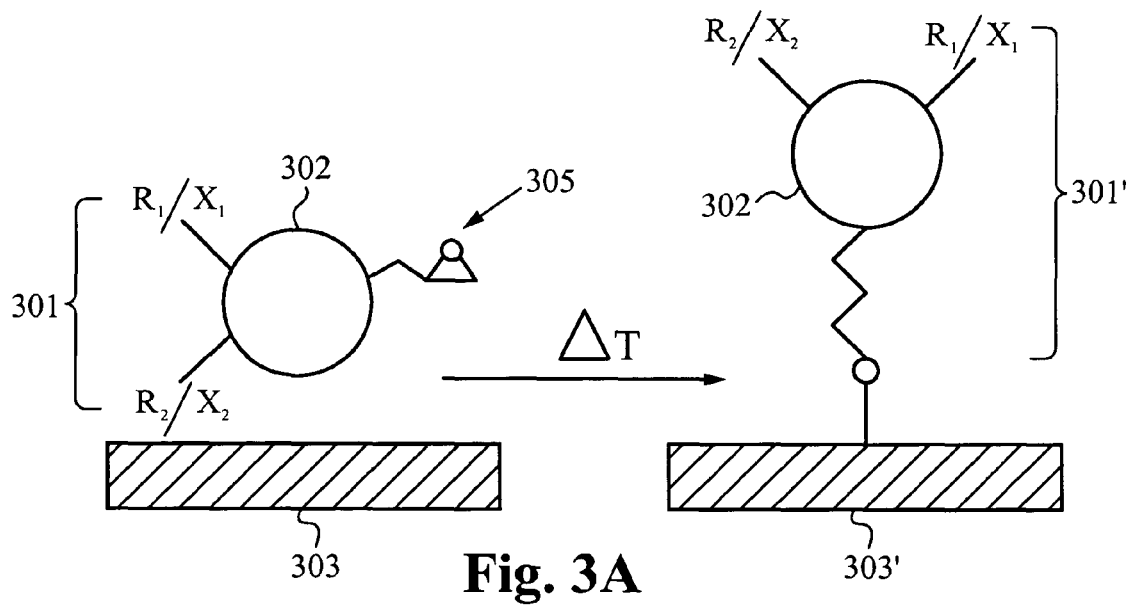
FIGS. 3A-B are schematic representations showing an N-Halamine hydantoinyl epoxide compound attaching to a surface of a material through a ring opening mechanism of the epoxide portion of the N-Halamine hydantoinyl epoxide compound.

Referring to FIG. 3A, a material 303 is functionalized with N-halamine hydantoinyl moieties 301' by adding one or more N-halamine hydantoinyl epoxide compounds 301 to the material 303 and curing the mixture of the material 303 and the one or more N-Halamine hydantoinyl epoxide compounds 301, such that the epoxide portion 305 opens and binds to the material 303 or surface of the material 303 and forms the functionalized material 303' with the N-halamine hydantoinyl moieties 301' attached thereto. The N-halamine hydantoinyl moieties 301' preferably include hydrogen groups $R_1$ and $R_2$ and oxidative halogen groups $X_1$ and $X_2$ or a combination thereof attached to the hydantoinyl portions 302 of the N-halamine hydantoinyl moieties 301'.

Figure 3B:
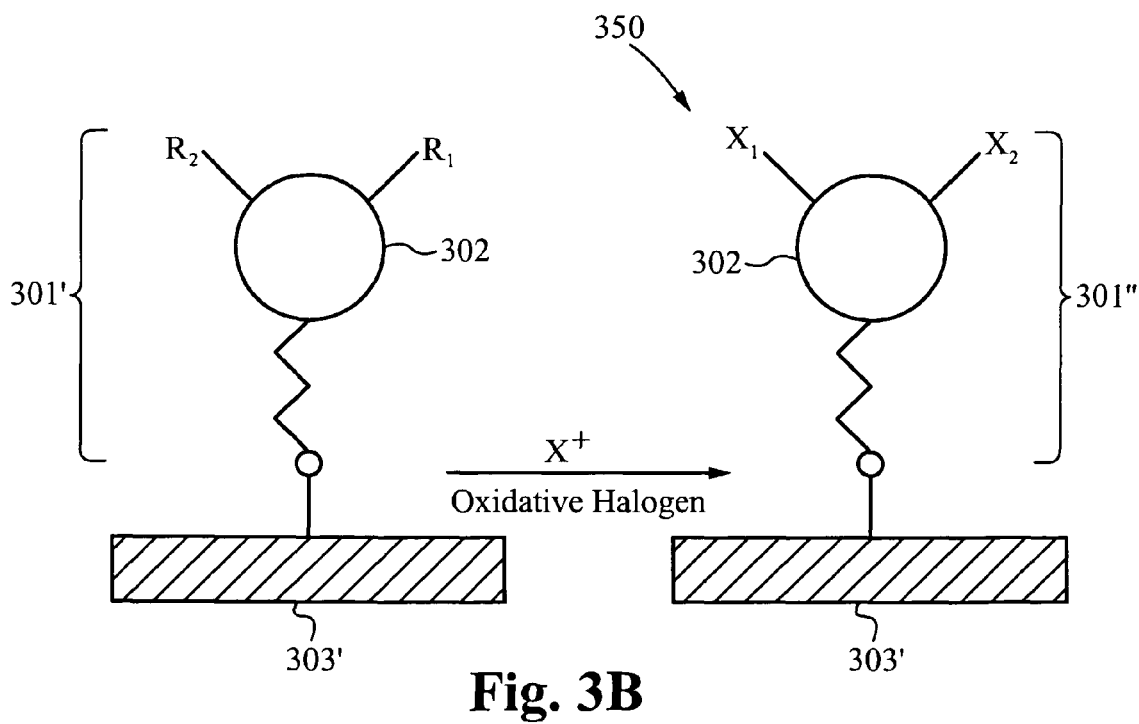

Now referring to the FIG. 3B, as described above, where the N-Halamine hydantoinyl moieties 301' can have hydrogen groups $R_1$ and $R_2$ attached thereto, the functionalized material 303' can be treated with a halogenating agent to replace a portion of the hydrogen groups $R_1$ and $R_2$ with oxidative halogen groups $X_1$ and $X_2$ and form a bocidal composition.

The unhalogenated hydantoinyl epoxide compounds can be synthesized by reacting the sodium or potassium salts of the appropriate hydantoin compounds with epichlorohydrin in water at ambient temperature for 6-10 hours. Some of the hydantoins such as 5,5-dimethylhydantoin and 1,3,8-triaza-7,7,9,9-tetramethylspiro[4.5]decane-2,4-dione, and the epichlorohydrin, can be obtained commercially from vendors such as the Aldrich Chemical Company in Milwaukee, Wis. The other hydantoin compounds can be prepared by reacting the appropriate dialkyl ketone with ammonium carbonate and potassium cyanide in a molar ratio of about 0.67:2.0:1.0, respectively, in a water/ethanol (1:1 by volume) solvent mixture at 50-60° C. for 4-10 hours. The alkali metal salts of the hydantoins can be prepared by mixing the dialkylhydantoins with equimolar quantities of either NaOH or KOH in water and stirring at ambient temperature for about 5-10 minutes. The hydantoinyl epoxide compounds can then be reacted with free chlorine or free bromine to produce the corresponding N-halaminehydantoinyl epoxide compounds which are biocidal, or they can be tethered to a surface or material before reaction with chorine or bromine to produce a biocidal surface or material in situ. The chlorinated compounds or surfaces/materials can be prepared by reacting the corresponding unhalogenated precursor compounds dissolved in water at ambient temperature with free chlorine from such sources as gaseous chlorine, sodium hypochlorite bleach, calcium hypochlorite, chloroisocyanurates, and dichlorohydantoins. In the case of the dichlorohydantoins, the chlorine moiety on the imide nitrogen should transfer to the more stable amide nitrogen of the hydantoinyl epoxide. Likewise, the brominated compounds or surfaces/materials can be prepared by exposing them in aqueous solution at ambient temperature to free bromine from such sources as molecular bromine liquid, sodium bromide in the presence of an oxidizer such as potassium peroxy monosulfate, and brominated hydantoins. Halogenation can also be effected in organic solvents employing free radical halogenating agents such as t-butyl hypochlorite.

The unhalogenated or halogenated hydantoinyl epoxides can be bound to a surface or material by exposing the surface or material to a solution of the unhalogenated hydantoinyl epoxide and then curing the surface or material at temperatures in the range of 0 to 300° C., more preferably 20 to 150° C., depending upon the nature of the surface or material, or by exposing the surface or material to a solution of the halogenated hydantoinyl epoxide at ambient temperature, and then exposing the surface or material to temperatures in the range of 0 to 60° C., more preferably 20 to 40° C., depending upon the nature of the surface or material, for curing purposes. The solvent for the coating process can be water or mixtures of water and organic solvents such as acetone, depending upon the solubility of the given hydantoinyl epoxide in water alone. Organic materials such as ethanol are less useful for the halogenated hydantoinyl epoxides because they partially protonate the nitrogen of the heterocyclic ring liberating halogen.

Dilute base can also be added to the aqueous solutions to enhance the opening of the epoxide ring moiety during bonding to the surfaces or materials. However, the epoxides should not be left in contact with a dilute base for extended periods in a bath before exposure to a surface or material because partial decomposition of the hydantoin ring may result. Also, the epoxides should not be left in contact with dilute acid for long periods in a bath before exposure to a surface or material because the diol which will slowly form will be less reactive with the surface or material than the epoxide.

Other additives can be introduced to the solutions of the hydantoinyl epoxides to enhance binding to the surface or materials, e.g. potassium thiocyanate for binding to cellulose. The solutions containing the copolymers can be exposed to the surfaces or materials by soaking, spraying, spreading, and the like. Following drying of the solution on the surface, curing at some temperature (the value of which depends upon the surface or material composition, e.g. 25° C. for paper, 95° C. for cotton fibers, etc.) for 15 to 30 minutes, should then be performed.

The surface or material can be rendered biocidal if the unhalogenated hydantoinyl epoxide were employed by exposure to a source of oxidative halogen, such as an aqueous solution of sodium hypochlorite bleach, calcium hypochlorite, chloroisocyanurates, and dichlorohydantoins, or an organic solution of t-butyl hypochlorite, for chlorination, or an aqueous solution of molecular bromine liquid, sodium bromide in the presence of an oxidizer such as potassium peroxy monosulfate, and brominated hydantoins for bromination. For example, an aqueous solution of 5 to 10% Clorox® can be used for efficient chlorination which can be accomplished at ambient temperature by spraying or soaking the surface or material with Clorox®. After halogenation, the surface or material should be rinsed with water and then allowed to dry in air at temperatures up to 40° C. (ambient temperature is preferable if time permits). The surface or material will then exhibit strong biocidal properties for various time periods dependent upon the composition of the surface or material, the use pattern (contact with organisms and halogen demand), the storage temperature, etc. When the bound halogen content becomes too low for efficient biocidal activity, the surface or material can be recharged with halogen in the same manner as for the original charging noted above.

An alternative means of attaching similar biocidal moieties to surfaces utilizing epoxide chemistry comprises first bonding an epoxide containing a substituted electrophilic alkyl functional group to the surface, and then bonding the heterocyclic N-Halamine or precursor N-halamine group to the already-tethered epoxide through nucleophilic substitution reactions. For example, epichlorohydrin could be used to bond the epoxide to the surface as disclosed in a permanent press application for cellulose in U.S. Pat. No. 2,985,501, and then the chloropropyl functionality thus tethered through the epoxide is reacted with the alkali metal salt of a 5,5-dialkylhydantoin to produce an anchored hydantoin which is halogenated in situ as described above to render the surface biocidal.

The mechanism of action of the biocidal surfaces and materials produced from the hydantoinyl epoxides described herein is believed to be a result of surface contact of the organism with chlorine or bromine moieties covalently bound to the heterocyclic functional groups on the bound hydantoinyl epoxide. The chlorine or bromine atoms are transferred to the cells of the microorganisms where they cause inactivation through a mechanism not completely understood, but probably involving oxidation of essential groups contained within the enzymes comprising the organisms.

A marked advantage of the biocidal surfaces and materials of this invention over prior technology is that they are much more effective biocidally against pathogenic microorganisms encountered in medical applications such as *Staphylococcus aureus* and *Pseudomonas aeruginosa* than are commercial biocides such as the quaternary ammonium salts, so they can serve a dual function: inactivation of disease-causing pathogens and of odor-causing microorganisms. For this reason the invention will have wide-spread use in medical settings such as hospitals, nursing facilities, and research laboratories. It should also be useful for biocidal applications in a variety of other industrial settings as well as in the home. A few examples of surfaces and materials which can be made biocidal with this invention include envelopes, surgical gowns and gloves, sheets, bandages, sponges, synthetic fibers, wood, chitin, chitosan, cement grout, latex caulk, acrylic films, paints, and polyurethanes.

The present invention is more particularly described in the following examples which are intended as illustrative only since numerous modifications and variations therein will be apparent to those skilled in the art.

EXAMPLES

Example 1

Preparation of Hydantoinyl Epoxides 5,5-Dialkylhydantoin derivatives are prepared by reaction of the appropriate dialkylketone with ammonium carbonate and either sodium or potassium cyanide in a molar ratio of about 0.67:2.0:1.0, respectively, in a water/ethanol (1:1 by volume) solvent mixture at 50-60° C. for 4-10 hours. For example, 5-methyl-5-propylhydantoin was prepared by first mixing 86.4 grams (0.90 mole) of ammonium carbonate with 29.3 grams (0.45 mole) of potassium cyanide in 125 mL of water in a 500 mL round-bottom flask. To this solution were added 25.8 grams (0.30 mole) of 2-pentanone in 125 mL of ethanol. The reaction mixture was heated to 50-55° C. while stirring for 6 hours. After cooling to ambient temperature, the reaction mixture was slowly poured into 200 mL of a 10% HCl solution. The resulting crude white solid product was collected by filtration and purified by recrystallization from a water/ethanol mix to produce 41.2 grams of white crystals (88% yield) which exhibited the following properties: mp 124-125° C.; $^1$H NMR (CDCl$_3$) ∂ 0.93 (t, 3H), 1.23-1.80 (m, 4H), 1.45 (s, 3H), 6.30 (s, 1H); $^{13}$C NMR (CDCl$_3$) ∂ 13.9, 16.9, 23.8, 39.9, 64.8, 156.2, 177.3; IR (KBr) 3233, 1767, 1712, 1433, 775, 449 cm$^{-1}$; m/z 156. Other 5,5-dialkylhydantoins were prepared by an analogous procedure, and their structures were verified by NMR, IR, and mass spectrometry. In this manner the ketones acetone, 2-pentanone, 2-octanone, acetophenone, benzophenone, cyclohexanone, and 2,2,6,6-tetramethyl-4-piperidone were employed to synthesize 5,5-dimethylhydantoin, 5-methyl-5-propylhydantoin, 5-hexyl-5-methylhydantoin, 5-methyl-5-phenylhydantoin, 5,5- diphenylhydantoin, 5-spiropentamethylenehydantoin, and 1,3,8-triaza-7,7,9,9-tetramethylspiro[4.5]decane-2,4-dione, respectively.

Then each of the 5,5-dialkylhydantoin derivatives, as well as spiropentamethylenehydantoin and 1,3,8-triaza-7,7,9,9-tetramethylspiro[4.5]decane-2,4-dione, were converted to their sodium or potassium salts by simply stirring them for 5-10 minutes in aqueous NaOH or KOH (equimolar mixture of base and hydantoin derivative). Then without actual isolation of the salts, the same molar concentration of epichlorohydrin was added to the solution, and the mixture was stirred for 6-10 hours at ambient temperature. For example, 0.05 mole of hydantoin derivative was mixed with 0.05 mole of NaOH in 40 mL of water in a 100 mL beaker. After stirring for 5-10 minutes at ambient temperature, 0.05 mole of epichlorohydrin was added followed by stirring for 6-10 hours at ambient temperature. Then most of the water was removed by evacuation, and 50 mL of acetone were added to dissolve the hydantoin epoxide derivative, which was then isolated by filtration of the NaCl byproduct and evaporation of the acetone solvent. The hydantoinyl epoxide derivatives were recovered as solids and/or oils and could be purified by column chromatography for spectroscopic characterization. The yields of the purified products were always at least 50%, but generally the crude products were used for the surface-binding studies.

Example 2

Chlorine Loadings on Dialkyhydantoinyl Epoxides Coated on Cotton

Solutions of the precursor hydantoinyl epoxide derivatives were prepared for use in coating onto cotton. The same molar concentration (0.26 mol/L) of each derivative was dissolved in a 1:1 by weight solution of acetone and water. Swatches of Style 400 Bleached 100% Cotton print Cloth (Testfabrics, Inc., West Pittston, Pa.) were soaked in each solution for 15 min and then cured at 95° C. for 1 h and then further at 145° C. for 20 min. Then the swatches were soaked in a 0.5% detergent solution for 15 min, rinsed several times with water, and dried in air at 70° C. The swatches were chlorinated by soaking them in a 10% solution of Clorox buffered to pH 7 at ambient temperature for 45 minutes, rinsed with water, and dried for 1 hour at 45° C. to remove any occluded free chlorine. An iodometric/thiosulfate titration was used to measure the weight percent of $Cl^+$ bound to each swatch of cotton. The results are shown in Table 1 below.

TABLE 1

Initial Chlorine Loadings on Dialkylhydantoinyl Epoxides Coated on Cotton from Baths Containing Equimolar Concentrations of the Epoxide Derivatives

| Dialkylhydantoinyl Epoxide Derivative | Initial Weight Percent of $Cl^+$ |
|---|---|
| Dimethyl | 0.15 |
| Methyl Propyl | 0.22 |
| Hexyl Methyl | 0.96 |
| Methyl Phenyl | 0.29 |
| Spirocyclohexyl | 0.16 |

These results are not easily rationalized. Several factors may be operable here including electronic and steric effects. The alkyl groups are all electron-donating substituents which should stabilize the N—Cl bonds; this effect should increase roughly with the number of carbon atoms in the alkyl group. Increased size of the alkyl groups should hinder the approach of water molecules in a hydrolysis process to remove the $Cl^+$ and to cause hydrolysis of the epoxide from the cellulose. Both arguments can rationalize why the dimethyl derivative either loads the least amount of chlorine and/or bonds the least firmly to the cotton. In any case, it is apparent that the capacity of the dialkylhydantoinyl epoxide derivatives bound to cotton to bind chlorine varies with the nature of the alkyl group, a fact which might be useful in tuning a particular structural group for a particular application. Two of the identical derivatives coated on cotton swatches were analyzed for chlorine content after 30 days of storage at ambient temperature from which room lighting was excluded. The dimethyl derivative then contained 0.10% by weight chlorine, and the methyl propyl derivative contained 0.16% by weight chlorine. However, after recharge using the procedure described above, the two derivatives contained 0.14 and 0.20% by weight chlorine, respectively, indicative of minimal loss of the hydantoinylepoxy coating.

Example 3

Stability toward Washing of Cotton Coated with 3-glycidyl-5,5-dimethylhydantoin

Swatches of Style 400 Bleached 100% Cotton print Cloth (Testfabrics, Inc., West Pittston, Pa.) were soaked in a 10% aqueous solution of 3-glycidyl-5,5-dimethylhydantoin containing 1% NaOH. The swatches were squeezed and cured at 65-70° C. for 80-90 minutes and then at 155-160° C. for about 5 minutes. After rinsing with water, the swatches were chlorinated in a 5% Clorox solution buffered to pH 7 for 50 minutes at ambient temperature. They were then rinsed with water and dried at 50° C. to remove occluded free chlorine. Weight percent $Cl^+$ was determined by iodometric/thiosulfate titration before and after standard washing cycles according to AATCC Test Method 61-1986. The results are shown in Table 2. These results clearly indicate that although the oxidative chlorine dissociates from the hydantoin ring during washing, the hydantoinyl moiety remains attached to the cotton through its condensation with the epoxide moiety, such that it can be recharged repeatedly with free chlorine (bleach). Furthermore, if bleach were added to each wash cycle, the coating could be maintained with oxidative chlorine, and hence remain biocidal, probably throughout the lifetime of the cotton fabric.

TABLE 2

Stability of Chlorinated 3-glycidyl-5,5-dimethylhydantoin-Coated Cotton Swatches to Washing Cycles

| Washing Cycles | $Cl^+$ % Remaining[a] | $Cl^+$ after % Recharge[b] | Chlorination after Washing Control Swatches (% $Cl^+$)[c] |
|---|---|---|---|
| 0 | 0.32 | | |
| 5 | 0.03 | 0.23 | 0.25 |
| 10 | 0.01 | 0.21 | 0.23 |
| 25 | 0.00 | 0.21 | 0.24 |
| 50 | 0.00 | 0.22 | 0.23 |

[a]The weight % Cl+ for chlorinated swatches before the indicated washing cycles.
[b]Rechlorination after washing swatches.
[c]Chlorination of washed unchlorinated swatches.

Similar washing testing was performed for the 5-methyl-5-phenyl, 5-hexyl-5-methyl, and 5-spiropentamethylene hydantoinyl epoxide derivatives coated on cotton swatches. Although higher initial chlorine loadings were obtained for all of these as compared to the 5,5-dimethyl derivative discussed above, there were greater losses of the hydantoinylepoxy coatings during washings as evidenced by lesser recharge abilities following 50 washing cycles.

Example 4

Stability of Chlorine on Polyester Coated with 3-glycidyl-5,5-dimethylhydantoin

In the case of polyester fabric (PET) (100% Dacron Type 54, Test Fabrics, Inc., Middlesex, N.J.), swatches were first treated with dilute NaOH (concentrations ranging from 0.5 to 2.0 N) at temperatures ranging from ambient to 100° C. for time periods of 5 to 60 min. After rinsing thoroughly with water, the swatches were soaked in an aqueous bath containing 9% by weight of 3-glycidyl-5,5-dimethylhydantoin at ambient temperature for 30 minutes. The swatches were then squeezed on a padding machine and dried at 60° C. for 60 minutes and cured at temperatures ranging from 75 to 175° C. for times ranging from 5 to 120 minutes. Chlorination was performed by soaking the treated fabric swatches in 10% Clorox solutions for 30 minutes. Then the swatches were thoroughly rinsed with water and dried in air at ambient temperature. The weight percent $Cl^+$ on the swatches was then determined by iodometric/thiosulfate titration at various times of exposure to ambient air in storage, and before and after washing tests conducted as described in Example 3. The 3-glycidyl-5,5-dimethylhydantoin adds to polyester fibers through disruption of a portion of the ester linkages, a process which is accelerated in the presence of dilute NaOH. The results of washing tests on the derivatized PET fibers are shown in Table 3. It is evident that pretreatment of the PET with dilute NaOH does enhance the loading of the epoxyhydantoin derivative on the material as evidenced by the increased loading of $Cl^+$. Furthermore, although the washing process causes the dissociation of bound chlorine from the PET, it can almost entirely be replenished by exposure to dilute bleach. In a practical use pattern, one should add dilute bleach into each wash cycle which should serve to maintain biocidal activity for the lifetime of the PET material. Finally, identical samples to those listed in Table 3 which had been pretreated with dilute NaOH were exposed to ambient air for 90 days. The losses of $Cl^+$ (in weight %) for the two types of samples were 0.19 to 0.11, and 0.21 to 0.12 over the 90 day period.

Example 5

Initial Chlorine Loading on 3-glycidyl-1,3,8-triaza-7,7,9,9-tetramethylspiro[4.5]decane-2,4-dione Coated on Cotton The hydantoinyl epoxide, 3-glycidyl-1,3,8-triaza-7,7,9,9-tetramethylspiro[4.5]decane-2,4-dione, synthesized by a procedure analogous to that outlined in Example 1, was coated onto cotton swatches. The coating bath contained 2.50 grams of the epoxide dissolved in 47.5 grams of a mixture of acetone and water (1:1 weight ratio). The cotton swatches (Style 400 Bleached 100% Cotton print Cloth (Testfabrics, Inc., West Pittston, Pa.)) were soaked in the solution for 15 minutes at ambient temperature, cured at 95° C. for 1 hour and then at 145° C. for 20 minutes, rinsed thoroughly with water, chlorinated with a 10% Clorox solution (buffered to pH 7) for 1 hour at ambient temperature, washed thoroughly with water, and dried at 45° C. for 1 hour. An iodometric/thiosulfate titration determined that the swatches contained 0.26% by weight $Cl^+$. Identical samples were stored for 30 days at ambient temperature in non-airtight bags in the absence of room lighting. At that point the samples contained 0.13% by weight titratable chlorine; however, after a recharge with chlorine as described above, they again contained 0.26% by weight chlorine. Thus, the coating remains intact and could be continually recharged with chlorine. Biocidal tests on cotton swatches, as described in the next example, revealed that the freshly chlorinated swatches provided a 6.6 log reduction (complete inactivation) of *S. aureus* and *E. coli* within 10 minutes of contact.

Example 6

Biocidal Efficacies of Chlorinated Hydantoinyl Epoxide Derivatives

Cotton swatches of area 2 square inches each (Style 400 Bleached 100% Cotton print Cloth (Testfabrics, Inc., West Pittston, Pa.) were soaked in coating baths containing several of the hydantoinyl epoxides (10% by weight for the chromatographically purified 5,5-dimethyl derivative in water containing 1% by weight NaOH; 0.02171 moles of the other crude derivatives, including the 5,5-dimethyl derivative, dissolved in 80 grams of a solution containing a mixture of acetone and water (1:1 by weight)) for 15 minutes and then cured at 95° C. for 1 hour and then further at 145° C. for 20 minutes. Then the swatches were soaked in a 0.5% detergent solution for 15 minutes, rinsed several times with water, and dried in air at 70° C. The swatches were chlorinated by soak-

TABLE 3

Stability toward Washing of Bound Chlorine on Hydantoinylepoxy-Derivatized Polyester (% $Cl^+$ Remaining)

| Washing Cycles | Pretreat in Water[a] % $Cl^+$ Left | After Recharge | Pretreat in NaOH[b] % $Cl^+$ Left | After Recharge | Pretreat in NaOH[c] % $Cl^+$ Left | After Recharge |
|---|---|---|---|---|---|---|
| 0 | 0.12 | | 0.19 | | 0.21 | |
| 5 | 0.01 | 0.09 | 0.01 | 0.16 | 0.01 | 0.17 |
| 10 | 0.00 | 0.09 | 0.01 | 0.15 | 0.01 | 0.17 |
| 25 | 0.00 | 0.09 | 0.00 | 0.15 | 0.00 | 0.17 |
| 50 | 0.00 | 0.07 | 0.00 | 0.14 | 0.00 | 0.16 |

[a]The PET was pretreated with a 10% solution of 3-glycidyl-5,5-dimethylhydantoin in water for 30 minutes.
[b]The PET was pretreated with a 10% solution of 3-glycidyl-5,5-dimethylhydantoin in a 1% solution of NaOH for 30 minutes.
[c]The PET was first soaked in a 1.0 N solution of NaOH at 60° C. for 60 min and then pretreated with a 10% solution of 3-glycidyl-5,5-dimethylhydantoin in a 1% solution of NaOH for 30 minutes.

ing them in a 10% solution of Clorox buffered to pH 7 at ambient temperature for 45 minutes, rinsed with water, and dried for 1 hour at 45° C. to remove any occluded free chlorine. An iodometric/thiosulfate titration was used to measure the weight percent of $Cl^+$ bound to each swatch of cotton. Unchlorinated cotton swatches and unchlorinated coated cotton swatches served as controls in the biocidal tests to be described below.

Biocidal efficacy tests were performed on the cotton swatches. Each swatch was inoculated with a 25 microliter drop of *Staphylococcus aureus* (ATCC 6538) containing $9.47 \times 10^6$ colony forming units (CFU). A second identical swatch was placed on top of the inoculated swatch as in a sandwich and was held in place by a steel weight. Following a specific contact time (5, 10, and 30 minutes) the bacterial cells were washed off the cotton with distilled, deionized water while vortexing, quenched with dilute sodium thiosulfate (0.02 N), and plated onto trypticase agar. Colony counts were performed after incubation at 37° C. for 24 and 48 hours. The results are shown in Table 4.

TABLE 4

Biocidal Efficacies against *S. aureus* for Dialkylhydantoinyl Epoxides Coated on Cotton

| Dialkylhydantoinyl-epoxide Derivative | Weight Percent Loading of $Cl^+$ | Contact Time (minutes) | Log Reduction of Bacteria |
|---|---|---|---|
| Cotton Control[a] | 0 | 5 | 0.66 |
| | 0 | 10 | 0.66 |
| | 0 | 30 | 0.74 |
| Dimethyl Control[b] | 0 | 5 | 0.81 |
| | 0 | 10 | 0.90 |
| | 0 | 30 | 1.01 |
| Dimethyl[c] | 0.44 | 5 | 3.81 |
| | 0.44 | 10 | 3.95 |
| | 0.44 | 30 | 6.98 |
| Dimethyl Control[d] | 0 | 5 | 0.79 |
| | 0 | 10 | 0.83 |
| | 0 | 30 | 1.05 |
| Dimethyl[e] | 0.15 | 5 | 1.68 |
| | 0.15 | 10 | 4.85 |
| | 0.15 | 30 | 4.85 |
| Methyl Propyl Ctl[d] | 0 | 5 | 0.65 |
| | 0 | 10 | 0.92 |
| | 0 | 30 | 0.97 |
| Methyl Propyl[e] | 0.22 | 5 | 3.62 |
| | 0.22 | 10 | 3.65 |
| | 0.22 | 30 | 6.98 |
| Spirocyclohexyl[d] | 0 | 5 | 0.77 |
| | 0 | 10 | 0.79 |
| | 0 | 30 | 0.85 |
| Spirocyclohexyl[e] | 0.19 | 5 | 3.58 |
| | 0.19 | 10 | 4.07 |
| | 0.19 | 30 | 6.98 |

[a]Uncoated cotton.
[b]Cotton coated with chromatographically purified 5,5-dimethyl derivative but not chlorinated.
[c]Cotton coated with chromatographically purified 5,5-dimethyl derivative which was chlorinated.
[d]Cotton coated with unpurified derivative but not chlorinated.
[e]Cotton coated with unpurified derivative which was chlorinated.

As can be seen from the results in Table 4, all of the chlorinated coatings provided complete inactivation of *S. aureus* within a contact time of 30 minutes except the unpurified dimethyl derivative which contained the lowest chlorine loading (0.15%). The purified dimethyl derivative did provide complete inactivation within a 30 minute contact time; it also provided the highest chlorine loading (0.44%). The chromatographic purification process is a bit tedious and would add additional expense to the coating process, so it may be desirable to use the crude, unpurified derivatives, perhaps at higher concentration, in the coating bath. It is evident that the control samples only provided about a loss of one Log of the bacteria; thus, most of the losses noted for the chlorinated samples can be attributed to true inactivation of the bacteria. Similar results were obtained for *E. coli* with a complete inactivation of this bacterium (6.65 logs) within 10 minutes contact for all derivatives tested. It can be concluded that the chlorinated hydantoinyl epoxide derivatives are biocidal and could be used to create biocidal cotton.

Example 7

1-Bromo-3-glycidyl-5,5-dimethylhydantoin Coated on Cotton

The hydantoinyl epoxide, 3-glycidyl-5,5-dimethylhydantoin, was coated onto cotton swatches. The coating bath contained a 5% by weight mixture of crude hydantoinyl epoxide in acetone and water (1:1 weight ratio). The cotton swatches (Style 400 Bleached 100% Cotton print Cloth (Testfabrics, Inc., West Pittston, Pa.)) were soaked in the solution for 15 minutes at ambient temperature, cured at 95° C. for 1 hour and then at 145° C. for 20 minutes, rinsed thoroughly with water, brominated with a 0.6% by weight unbuffered aqueous solution of liquid bromine for 1 hour at ambient temperature, washed thoroughly with water, and dried at 45° C. for about 30 minutes. An iodometric/thiosulfate titration determined that the swatches contained 0.25% by weight $Br^+$. Identical samples were stored for 30 days at ambient temperature in the absence of room lighting. At that point the samples contained no titratable bromine; however, after a recharge with bromine as described above, they again contained 0.25% by weight bromine. Thus, although the N—Br bond on the hydantoin ring dissociates much more rapidly than a corresponding N—Cl bond, the coating remains intact and could be continually recharged with bromine. Biocidal tests on cotton swatches, as described in the previous example, revealed that the freshly brominated swatches provided a 6.6 log reduction (complete inactivation) of *S. aureus* and *E. coli* within 30 minutes and 10 minutes, respectively. N-bromamines are always more biocidal than their N-chloramine counterparts, but the increased stability of the N-chloramines as compared to the N-bromamine counterparts can render the N-chloramine derivatives more effective in a particular use pattern.

Although the present invention has been described with reference to specific details of certain embodiments thereof, it is not intended that such details should be regarded as limitations upon the scope of the invention except as and to the extent that they are included in the accompanying claims.

What is claimed is:

1. A method for rendering a material biocidal, the method comprising:
    a) adding an N-halamine or a precursor of N-halamine comprising a hydantoinyl portion and an epoxide portion to the material, wherein the N-halamine or the precursor of N-halamine is a hydantoinyl epoxide having a structure:

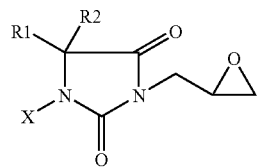

and wherein $R_1$ and $R_2$ are one or more of $C_1$-$C_8$ alkyl groups, methyl groups, cycloalkyl groups and phenyl groups and X is one of H, Cl, and Br; and b) curing the N-halamine or the precursor of N-halamine with the material, such that the epoxide portion opens and attaches the hydantoinyl portion to a portion of the material.

2. The method of claim 1, further comprising adding a halogen solution.

3. The method of claim 2, wherein the halogen solution is added prior to the step of curing the N-halamine and the material.

4. The method of claim 2, wherein the halogen solution is added after the step of curing the N-halamine and the material.

5. The method of claim 1, wherein the material is selected from the group consisting of cellulose, chitin, chitosan, synthetic fibers, cement grout, latex caulk, acrylic film, polyurethane, plastics and paint.

6. A composition comprising hydantoinyl epoxide structures that are bound to a material through oxygen atoms of epoxide moieties of the hydantoinyl structures, wherein the hydantoinyl epoxide has the structure:

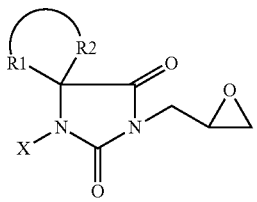

and wherein $R_1$ and $R_2$ are one or more of $C_1$-$C_8$ alkyl groups, methyl groups, cycloalkyl groups and phenyl groups and X is one of H, Cl, and Br.

7. The composition claim 6, wherein the hydantoinyl structures are halogenated.

8. The composition of claim 7, wherein the hydantoinyl structures are halogenated through nitrogen atoms of the hydantoinyl structures.

9. The composition of claim 6, wherein material includes one or more of cellulose, chitin, chitosan, synthetic fibers, cement grout, latex caulk, acrylic film, polyurethane, plastics and paint.

10. A composition comprising hydantoinyl epoxide structures that are bound to a material through oxygen atoms of epoxide moieties of the hydantoinyl structures, wherein the hydantoinyl epoxide has the structure:

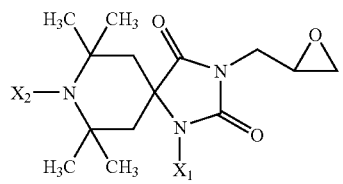

and wherein $X_1$ and $X_2$ are a H, Cl, and Br groups or a mixture thereof.

11. The composition of claim 10, wherein the hydantoinyl structures are halogenated.

12. The composition of claim 11, wherein the hydantoinyl structures are halogenated through nitrogen atoms of the hydantoinyl structures.

13. The composition of claim 10, wherein the material includes one or more of cellulose, chitin, chitosan, synthetic fibers, cement grout, latex caulk, acrylic film, polyurethane, plastics and paint.

* * * * *

UNITED STATES PATENT AND TRADEMARK OFFICE
CERTIFICATE OF CORRECTION

PATENT NO. : 8,821,907 B2
APPLICATION NO. : 11/373458
DATED : September 2, 2014
INVENTOR(S) : S. D. Worley et al.

Page 1 of 1

It is certified that error appears in the above-identified patent and that said Letters Patent is hereby corrected as shown below:

In the Claims

Column 14, Lines 15-22, please replace the figure of Claim 10, with the following figure:

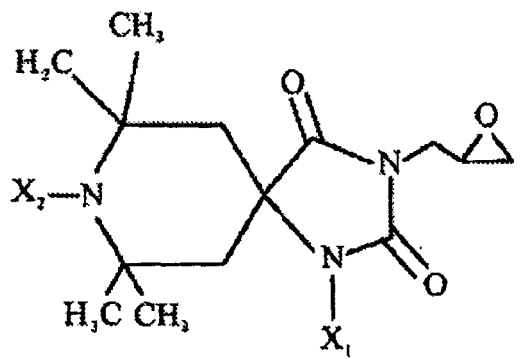

Signed and Sealed this
Tenth Day of March, 2015

Michelle K. Lee
*Deputy Director of the United States Patent and Trademark Office*